(12) United States Patent
Myszka et al.

(10) Patent No.: US 8,211,382 B2
(45) Date of Patent: Jul. 3, 2012

(54) MICROASSAY WITH INTERNAL REFERENCING

(75) Inventors: David Myszka, Salt Lake City, UT (US); Bruce Kent Gale, Taylorsville, UT (US); Joshua Wayne Eckman, North Salt Lake, UT (US); Sriram Natarajan, Bridgewater, NJ (US)

(73) Assignee: Wasatch Microfluidics, LLC, Salt Lake City, UT (US)

( * ) Notice: Subject to any disclaimer, the term of this patent is extended or adjusted under 35 U.S.C. 154(b) by 301 days.

(21) Appl. No.: 12/564,448

(22) Filed: Sep. 22, 2009

(65) Prior Publication Data

US 2010/0075860 A1    Mar. 25, 2010

Related U.S. Application Data

(60) Provisional application No. 61/099,091, filed on Sep. 22, 2008.

(51) Int. Cl.
*C40B 30/00* (2006.01)
*C40B 60/12* (2006.01)

(52) U.S. Cl. ............ 422/408; 422/402; 422/403; 506/7; 506/30; 506/39

(58) Field of Classification Search .......... 422/502–507; 506/7–9, 33–40; 435/283.1–288.5; 436/6, 436/111, 501
See application file for complete search history.

(56) References Cited

U.S. PATENT DOCUMENTS

| | | | |
|---|---|---|---|
| 6,110,426 A | 8/2000 | Shalon et al. | |
| 6,365,349 B1 | 4/2002 | Moynihan et al. | |
| 6,391,625 B1 | 5/2002 | Park et al. | |
| 6,503,715 B1 | 1/2003 | Gold et al. | |
| 6,623,696 B1 | 9/2003 | Kim et al. | |
| 6,733,968 B2 | 5/2004 | Yamamoto et al. | |
| 2003/0068253 A1 | 4/2003 | Bass et al. | |
| 2004/0014102 A1 | 1/2004 | Chen et al. | |
| 2005/0106621 A1 | 5/2005 | Winegarden et al. | |
| 2007/0087348 A1* | 4/2007 | Notcovich et al. | ................. 435/6 |
| 2007/0199642 A1 | 8/2007 | Natarajan | |
| 2007/0231458 A1 | 10/2007 | Gale et al. | |
| 2007/0231880 A1 | 10/2007 | Chang-yen et al. | |

FOREIGN PATENT DOCUMENTS

| | | |
|---|---|---|
| JP | 10084639 | 10/1999 |
| WO | WO 2006/014460 | 2/2006 |

* cited by examiner

*Primary Examiner* — In Suk Bullock
*Assistant Examiner* — Timothy G Kingan
(74) *Attorney, Agent, or Firm* — Thorpe North & Western LLP

(57) ABSTRACT

Specialized microfluidic networks are utilized to deposit substances on sensor surfaces. In particular, a flow-based microfluidic printhead is used as an interface to deliver multiple analytes to a sensor for simultaneous analysis. Furthermore, internal referencing is incorporated into sensor regions for improved sensitivity.

32 Claims, 5 Drawing Sheets

MICROASSAY WITH INTERNAL REFERENCING

The present application claims the benefit of U.S. Provisional Patent Application No. 61/099,091, filed on Sep. 22, 2008, the entirety of which is incorporated herein by reference.

BACKGROUND

An increasing number of sensing and imaging platforms are available for sensing biomolecular interactions, particularly those interactions that are useful in assaying analytes of interest. Biosensors based on microarrays provide assaying platforms that are compact, require smaller samples, and are capable of increased throughput. Throughput and efficiency of microarray biosensors can be greatly increased by the use of microfluidics technologies to deliver sample fluids to deposition sites and create high-density arrays. However, for many sensor platforms to significantly compete for biomarker screening, drug discovery, and other clinical diagnostic applications, there is a need for improved sensitivity and improved ability to distinguish non-specific binding.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
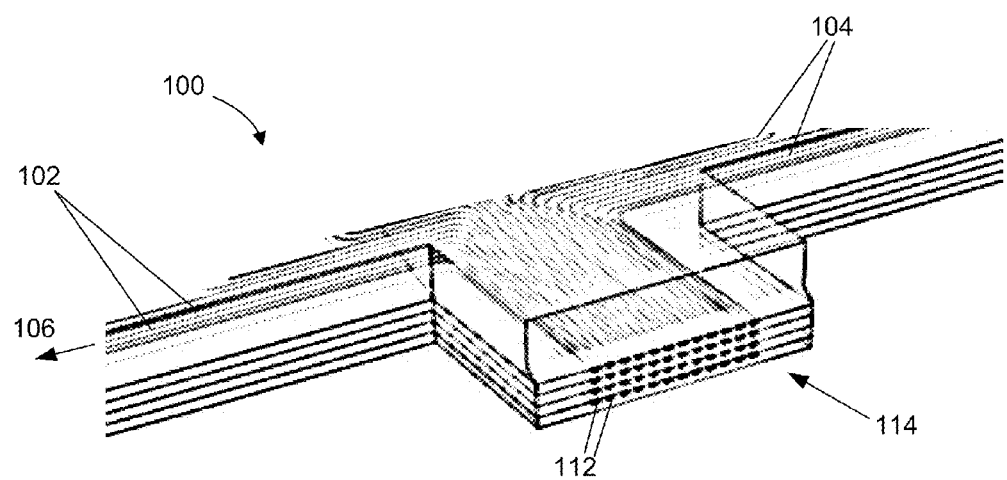
FIG. 1 is a perspective view diagram of a microfluidic spotter in accordance with an embodiment of the present disclosure.

Reference will now be made to the exemplary embodiments illustrated, and specific language will be used herein to describe the same. It will nevertheless be understood that no limitation of the scope of the invention is thereby intended.

DETAILED DESCRIPTION

In describing embodiments of the present disclosure, the following terminology will be used.

The singular forms "a," "an," and "the" include plural referents unless the context clearly dictates otherwise. Thus, for example, reference to "a needle" includes reference to one or more of such needles and "etching" includes one or more of such steps.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data (numbers of elements, amounts, dimensions, etc.) may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "50-250 micrometers" should be interpreted to include not only the explicitly recited values of about 50 micrometers and 250 micrometers, but also include individual values and sub-ranges within the indicated range. Thus, included in this numerical range are individual values such as 60, 70, and 80 micrometers, and sub-ranges such as from 50-100 micrometers, from 100-200, and from 100-250 micrometers, etc. This same principle applies to ranges reciting only one numerical value and should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall expressly include "exactly," consistent with the discussion above regarding ranges and numerical data.

With these definitions in mind, the present disclosure is drawn to methods and systems for performing a microassay. In one embodiment, a method for patterning a surface for a microassay can comprise providing a spotter including at least one fluid pathway adapted to provide a printing cavity having a printing orifice and an interrogation cavity having an interrogation orifice, both the printing orifice and the interrogation orifice being configured to form a seal with the surface;

and placing the spotter against the surface so as to seal the printing orifice to the surface and form a printing flow chamber defined by the printing cavity and the surface. Additional steps include flowing a fluid (including a capture substance or a sample fluid) through the printing flow chamber so as to print a spot onto the surface, and relocating the spotter along the surface over a distance and in a direction so that the interrogation orifice overlaps both a portion of the spot and an adjacent unprinted space of the surface. Another step can comprise placing the spotter against the surface, thereby resealing the interrogation orifice to the surface to form an interrogation flow chamber defined by the interrogation cavity and a second location on the surface. The second location can be positioned over both a portion of the spot and an adjacent unprinted space. In one embodiment, the printing flow chamber and the interrogation flow chamber can be provided by the same structure. It is noted that the fluid can include a capture substance and the second fluid can include a sample fluid (where the presence or concentration of analyte is being tested), or vice versa.

In another embodiment, a method for performing a microassay with internal referencing can comprise providing a spotter comprising a fluid pathway including a cavity that comprises an orifice adapted to form a seal with the surface, and placing the spotter against the surface so as to seal the orifice to the surface and form a first printing flow chamber defined by the cavity and the surface. Other steps can include flowing a first fluid containing a first substance through the first printing flow chamber so as to print a first spot of the first substance onto the surface; relocating the spotter along the surface over an adjacent space relative to the first spot, and optionally partially over the first spot; and placing the spotter against the surface so as to seal the orifice to the surface and form a second printing flow chamber defined by the cavity and the surface. Additional steps can include flowing a second fluid containing a second substance through the second printing flow chamber so as to print the second substance to form a second spot; relocating the spotter along the surface so that the orifice overlaps both a portion of the first spot and a portion of the second spot; placing the spotter against the surface so as to seal the orifice to the surface and form an interrogation flow chamber defined by the cavity and the surface; and flowing a sample fluid through the interrogation flow chamber so that the sample fluid encounters both the portion of the first spot and the portion of the second spot.

In another embodiment, a method of performing a microassay on surface can comprise steps of providing a spotter including at least one fluid pathway adapted to provide a printing cavity having a printing orifice and an interrogation cavity having an interrogation orifice, both the printing orifice and the interrogation orifice being configured to form a seal with the surface. Additional steps can include placing the spotter against the surface so as to seal the printing orifice to the surface and form a printing flow chamber defined by the printing cavity and the surface, and flowing a fluid including a capture substance through the printing flow chamber so as to print a spot including the capture substance onto the surface. Still further steps can include relocating the spotter along the surface over a distance and in a direction so that the interrogation orifice overlaps both a portion of the spot and an adjacent unprinted space of the surface, and placing the spotter against the surface so as to seal the interrogation orifice to the surface to form an interrogation flow chamber defined by the interrogation cavity and a second location on the surface, said second location being positioned over both a portion of the spot and an adjacent unprinted space. An additional step can also include flowing a sample fluid through the interrogation flow chamber so as to generate contact between the second fluid and both the portion of the spot and the unprinted space.

In still another embodiment, a system for performing a microassay with internal referencing can comprise a spotter comprising a fluid pathway including a cavity with an orifice adapted to form a seal with a surface and to form a spot on the surface within the orifice. The system can also comprise a manipulator operably connected to the spotter and adapted to seal, relocate, and re-seal the orifice against the surface. The re-seal of the orifice on the substrate can be carried out by relocating the cavity from a location of the seal over a distance and in a direction so that the orifice overlaps both a portion of the spot and an adjacent unprinted space of the surface.

Spotters generally for patterning microarrays are described in detail in International Patent Application No. WO 2006/014460, which is incorporated herein by reference in its entirety. Such a spotter increases the surface density at each spot by directing a flow of the desired substance, such as probes and/or target compounds, over the spot area until a high-density spot has been created. Examples of probes that may be flowed over a surface include: proteins; nucleic acids, including deoxyribonucleic acids (DNA) and ribonucleic acids (RNA); cells; peptides; lectins; modified polysaccharides; synthetic composite macromolecules; functionalized nanostructures; synthetic polymers; modified/blocked nucleotides/nucleosides; synthetic oligonucleotides; modified/blocked amino acids; fluorophores; chromophores; ligands; chelates; haptens; drug compounds; antibodies; sugars; lipids; liposomes; tissue; viruses; any other nano- or microscale objects; and any combinations thereof. As a substance flows over the surface of the microarray substrate, it may bind or adsorb to a surface of the substrate, depending on the chemistry involved in the system.

Figure 2:
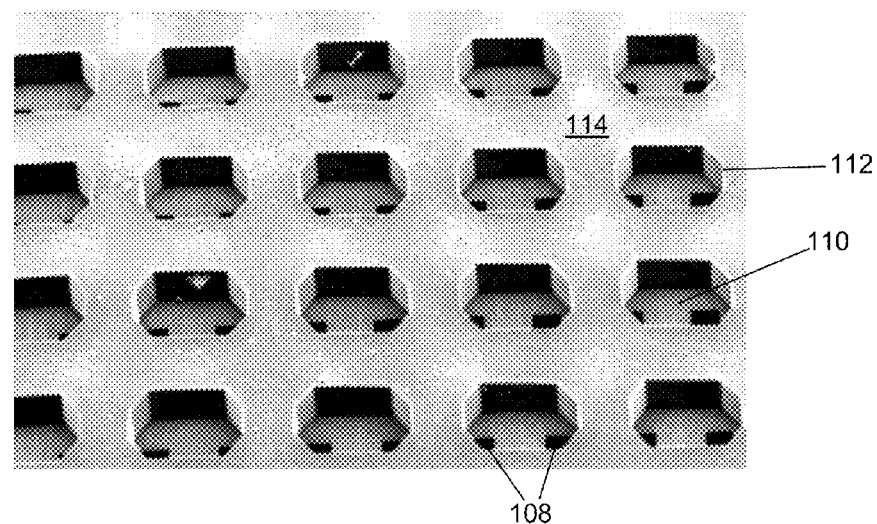
FIG. 2 is a scanning electron micrograph providing a perspective view of a face of a spotter in accordance with the embodiment in FIG. 1, particularly the orifices and cavities disposed therein.

An exemplary embodiment of a spotter in accordance with the present disclosure is shown in FIGS. 1-2, where FIG. 1 is a perspective view of the apparatus and FIG. 2 provides a close up view of a face of the spotter. The spotter 100 comprises a plurality of fluid pathways, wherein a fluid pathway comprises at least a cavity through which a fluid passes and an orifice included in the cavity by which the fluid is exposed to a surface of an analysis platform. In a more detailed embodiment, each pathway comprises a first conduit 102 and a second conduit 104, the first and second conduit each having a proximal end 106 and a distal end 108, wherein the distal end of the first conduit is operably connected to the distal end of the second conduit via a cavity 110, and wherein an orifice 112 of the cavity opens onto a face 114 of the spotter. An array of orifices in the face of a spotter are clearly shown in FIG. 2. The cavities 110 and distal ends 108 of conduits leading into the cavities are also visible in FIG. 2.

The orifice 112 is operable to form a seal with a surface onto which spotting is to be done. When such sealing is accomplished, the cavity 110 and the surface sealed thereunder form a flow chamber through which fluid from the first conduit 102 can flow, contacting the substrate surface before leaving the chamber by the second conduit 104. Therefore, the plurality of the orifices are configured in a static array adapted to dispose fluid on the surface of a substrate. The fluid pathways are configured such that a fluid may flow through the first and second conduits, contacting the surface of a substrate, when the orifice is sealed against the surface. According to some embodiments, the direction of fluid flow may be reversible, so that a bolus of fluid may flow from the first conduit, into the cavity, and into the second conduit, or the fluid may flow through these components in the reverse order. According to other embodiments, the conduits may be operably connected to a common reservoir, allowing a bolus of fluid to pass through the cavity multiple times in the same direction. In an alternate embodiment, a given volume of fluid passes through the cavity only once.

In accordance with embodiments of the present disclosure, conduits provide a means of conveying a fluid (and thereby a substance of interest carried by the fluid) to a region of interest. Conduits may also be referred to as channels, microchannels, canals, microcanals, microtubules, tubules and/or tubes, where the terms are used to describe a fluid pathway. The term "inlet conduit," "inlet microchannel," or "inlet microtubule" may be either the first or second conduit and the terms "outlet conduit," "outlet microchannel," or "outlet microtubule" may be the alternative conduit of the pathway. In some embodiments (described above) the conduit that serves as the inlet conduit varies as a substance flows back and forth between the conduits. For the purpose of describing the invention, "inlet" or "outlet" is may be used to reference the proximal end of the respective conduit.

As will be apparent in light of the present disclosure, the inlet and outlet (first and second) conduits may be essentially a single curved channel with a hole (orifice) in the channel for depositing substances on the substrate. However, for the purpose of describing the present invention, instead of referring to these embodiments as having a single channel or conduit, a "set" or "pair" of conduits is used to describe the channel with the orifice typically providing the division point. As discussed herein, a wide variety of connections between a set of channels (e.g., microchannels), and a wide variety of means for forming an orifice, are possible.

The cavities 110 may have a wide variety of shapes and incorporate numerous structures. The cavities may be formed separately from the conduit or formed by the conduit, and may be designed with flow constriction and turbulence inducers to create different flow patterns and shear forces across a spotted area on a substrate. Embodiments in which only one substance is flowed at a time may be used for sequential processing of the spot with different substances. This can be achieved by passing substances sequentially through a single inlet microchannel or, alternatively, more than two inlet microchannels may be connected to a cavity. Furthermore, two conduits do not have to physically connect to form a conduit.

Substances may be moved through the spotter conduits either by pressure-flow, gravity-flow, electrokinetical means, air pressure, any other suitable means, or combinations thereof. Numerous ways for creating pressure-flow and gravity-flow are known, for example, pumps and vacuums. If the proximal end of an outlet conduit is lower than the proximal end of the corresponding inlet conduit a siphon may be established for flowing a substance through the spotter. Many of the substances that may be flowed through the conduits are charged, e.g., DNA having a negative charge, therefore, electrokinetic pumps may be used to move charged substances within the conduits. Air pressure may be used, for example, to push a plug of a viscous gel along the fluid pathway to propel a solution or a reservoir may be pressurized to propel the solution. Additionally, it may desirable to dope or coat the interior of the conduits to increase the negative charge of the conduits, which will reduce the friction between negatively-charged substances and the interior of the conduits.

The spotter face 114 refers to the spotter surface that mates with a substrate upon which a substance is to be flowed, such as a microarray substrate. As can be seen in FIG. 2, the spotter face may be a flat surface regardless of the number of orifices included within the spotter. Viewing the spotter face in the horizontal plane, when it is desired that the spotter face be a flat surface it is preferable that the orifices deviate from each other less than 1 mm in the vertical plane, even more preferable less than 100 microns, even more preferable less than 50 microns, even more preferable less than 20 microns, and even more preferable less than 5 microns.

However, the spotter face 114 need not be a flat surface. For example, the spotter face can merely be the orifices of the distal ends of a bundle of microtubules. In this embodiment, if the orifices are circular, the spotter face will be a collection of rings. In a bundle of microtubules, gaps, rather than a solid surface, may be present between the outer edges of the orifices. These gaps may also be filled in, if desired, by methods known in the art. For example, in the microtubule embodiment, the microtubules may be held together by an epoxy used to fill in the gaps between the channels. The cured epoxy and channels may then be cut and/or polished to form a smooth surface.

The spotter face 114 can be so configured that when the face is pressed against a substrate surface, a fluid-tight seal should form, so that each cavity 110 becomes a sealed chamber defined by the walls of the cavity and the area of substrate surface onto which the cavity opens. That is, the spotter face can be so configured that pressing it against the substrate is sufficient to create the fluid-tight seal. The seal insures that a fluid moving through the conduit into each cavity/chamber contacts only the area of substrate constituting the floor of the chamber, without escaping to surrounding areas. This also insures that portions of the surface against which the face is pressed (but are not exposed to a cavity) will receive no contact with the fluid and therefore be substantially free of any binding substance in the fluid. This feature facilitates the internal referencing feature that will be described further below.

Figure 3:
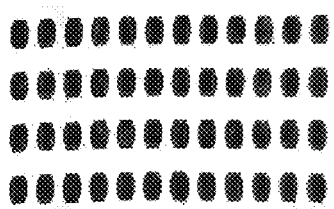
FIG. 3 is a view of a face of the spotter of FIG. 2 that has been sealed to a surface plasmon resonance imaging (SPRi) sample platform.

The spotter face 114 may be any size or geometry. The spotter face may be designed to cover a 76 cm×26 cm microscope slide, or even a 25 mm, 50.8 mm, 76.2 mm, 100 mm, 125 mm, 150 mm, 200 mm, or 300 mm wafer. Additionally, the spotter face can be designed to correspond to any substrate or structure on a substrate. For example, if a substrate has ridges, the spotter face may be modified to have valleys that mate with the substrate ridges or visa versa. The spotter face may also be made rigid or of sufficient flexibility to conform to a substrate surface. In some embodiments, the spotter face is designed so as to facilitate integrating the spotter with an analysis platform. For example, the spotter may be designed so as to seal effectively onto a substrate that can serve as the transducer face of known analysis platforms such as a surface plasmon resonance imaging (SPRi) platform. FIG. 3 provides an underside view of the glass sample platform of an SPRi system, to which a spotter face that has been sealed to form an array of sealed chambers (these appear in the figure as black spots).

Any number of devices may be attached to the spotter. A few examples are pumps, blowers, vacuums, fluid lines, heating/cooling jackets, mounting hardware, and reservoirs such as beakers or microtiter plates. All of the outlet microchannels may return to the same reservoir from which all of the inlet microchannels feed. In this way, increased binding of a molecule in the spot may be possible even with fluids in which the molecule is present in very low concentrations. Or each inlet microchannel may feed from a unique reservoir where only a single outlet microchannel returns to that reservoir, or there may be no return flow to that reservoir from an outlet microchannel. Any number of variations is possible and is within the scope of the disclosure.

The spotter of the disclosure provides each spot with its own individually addressed microfluidic channels, and a large number of spot arrays can be addressed in parallel. Constant substance flow can be maintained for an extended period of time to allow spotted areas to build a high-density spot. This technique allows for much higher signals to be generated than when standard concentrations are used with traditional spotters. The higher signals increase the signal-to-noise ratio, and thereby allow better data to be collected. Lower concentration solutions may also be used with the spotter and still yield satisfactory results, which can result in more efficient use of scant materials. A few examples of assays that may be conducted on an array are fluorescence spectroscopy, chemiluminescence detection, color-staining, other optically-based microarray sensing technologies, or radiometrics.

The spotter may be used to produce two-dimensional arrays. The spotter thus has the potential to fabricate microarrays with an unlimited number of defined spots, with each spot individually tailored to a specific deposition density. The spotter may also sequentially chemically process individual spots, either through the use of the same spotter or through multiple spotters. The spotter may be used to perform layer-by-layer self-assembly (LBL) to build up spot concentration. Multiple layering and washings on the spotted area may be performed simply by changing the substance that is flowed over the spot. Additionally, the surface of the substrate may be modified by flowing the appropriate material through the spotter. Surface modification of the internal walls of a spotter microchannel may be performed using solutions, such as BSA (bovine serum albumin) to reduce binding of a substance. In an exemplary embodiment, the spotter is a disposable spotter, thereby eliminating contamination issues.

Multiple layering approaches are particularly useful in biosensors and other microanalysis platforms in which a substrate surface must be chemically prepared for detection of a particular substance. For example, a sensor array for interrogation by a potential analyte may be made by functionalizing spots with molecules of a capture substance for which the analyte has a high binding affinity. A method of employing this approach can involve using a spotter having at least one cavity as described herein in steps including (a) sealing the spotter to a suitable substrate so as to create at least one flow chamber; (b) flowing a fluid containing a capture substance through the flow chambers so as to create at least one spot comprising a surface printed with the capture substance; (c) flowing a fluid potentially containing analytes that may bind with the capture substance. Accordingly the flow chamber may be referred to according to its role, i.e. a printing flow chamber when printing a spot, an interrogation flow chamber when interrogating a printed spot, and so forth. The spotter disclosed herein allows for high throughput analysis, including simultaneous creation of a large array of printed spots and also simultaneous interrogation of the spots with identical or different samples.

In accordance with the present disclosure, a substance flows through the inlet microchannel in the spotter, to the orifice, contacting the surface of the substrate, and then through the outlet microchannel in the spotter. This flow path provides an opportunity for substances to bind or adsorb to the surface depending on the chemistry involved in the system. As used herein, the term "bind" refers to binding, adhesion, adsorption, association, or any other chemical or mechanical process for retaining a substance at a substrate. Specific binding is used to refer to a substance, such as a protein, being binding to a surface in a non-random fashion. "Non-specific binding" refers to undesirable or uninformative binding or adhesion, as understood in the art. By way of example, non-specific binding can describe binding of a molecule of interest to a surface not specifically activated for such binding. A more typical example of non-specific binding refers to binding by species of molecules beside the species of interest. These examples are mentioned by way of illustration, and are not intended to be limiting. In either case, non-specific binding of substances can produce a binding-related signal that may be detectable by an assay technique but which provides little to no useful information.

Preferably, the spotter allows for fabrication of spots with low cross-talk and low background noise, due to the sealing of the surface of the microassay with the spotter orifices. As such, an array created with such a spotter can include discrete and well-defined spots corresponding to the positions of the flow chambers, as well as spaces adjacent to each spot, said spaces having received little or no contact with any of the substances used in spotting. These spaces can provide a reference against which to evaluate any binding that occurs in the spots. Accordingly, the present disclosure generally provides for methods of microanalysis using unprinted areas as a reference. An effective way of using these spaces as a reference can include interrogating a spot and an adjacent unprinted space with the same sample solution. Then both locations can be analyzed in parallel. Any binding that occurs in the spot can be compared to any binding detected in the unprinted space. During interrogation, any binding that is not specific to the printed capture material may occur in both the printed spot and the unprinted space. Such non-specific binding can be accounted for by generating a signal that corresponds to binding density and then comparing the signal from the printed spot with that from the unprinted spot. In a more particular approach, the signal from the unprinted space is subtracted from the signal detected in the printed spot. This approach can also be used to correct for any artifactual signal that is not associated with binding but is rather produced by the substrate surface itself.

Figure 4:
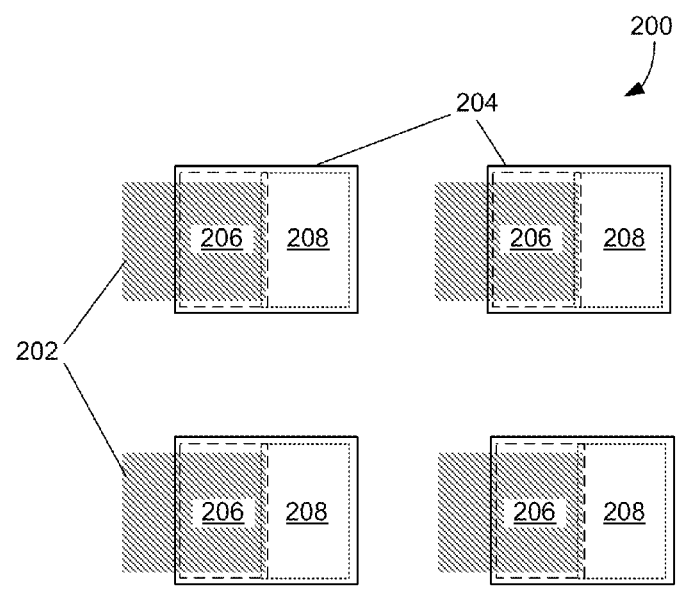
FIG. 4 is a diagram illustrating an array printed with a spotter in accordance with an embodiment of the present disclosure, showing the location of flow chambers after relocating the spotter.

Correction by reference can be made more effective if a printed spot and an unprinted space can be interrogated by the same bolus of sample fluid. This insures that both surfaces are contacted by identical samples, and reduces concerns arising from possible variation among samples. Accordingly, the present disclosure provides methods and systems for microanalysis with correction using an internal reference. In one embodiment, a spotter is used as described herein to print a spot of a capture substance onto a surface. A capture substance is chosen that reacts with a molecule of interest, so that said molecules contacting the surface will bind or otherwise adhere to the surface. The spotter is then moved a distance and in a direction and placed on the surface again so the cavity is now exposed to both a part of the spot and an unprinted area of the surface. In a particular aspect, the spotter is moved laterally over a distance roughly equal to one-half the width of the spot before resealing, so that now roughly half of the printed spot is sealed under the cavity. In another aspect, the spotter is moved a distance so that upon re-sealing, the cavity forms a flow chamber in which about half of the floor is printed surface and about half is unprinted surface. An array 200 of spots 202 printed in accordance with this embodiment is illustrated in FIG. 4. In this array it can be seen that after an initial printing, the spotter has been relocated on the surface so as to establish new flow chambers, the outlines 204 of which are indicted by the solid rectangles. These new flow chambers partially overlap with the initially printed spots, so that roughly one-half of the floor of each chamber is pre-printed surface 206, and the remainder is unprinted surface 208. A sample fluid is then flowed through the flow chamber so that both the printed and unprinted surface is contacted by the fluid.

Any binding in the printed area can then be corrected for non-specific binding. The method of correction will depend on the type of assay used and the platform used for detection and analysis of binding. For example, when used in conjunction with SPRi, the spotter is used to print an array of functionalized spots on a substrate. A typical substrate used in SPRi is a glass slide coated with gold film and optionally an additional layer of dextran. Functionalization may be provided by using the spotter to flow one or more molecules chosen to create a surface that will bind the molecule of interest. The spotter is then shifted and used to interrogate printed and unprinted surface. As the sample fluid passes through the chamber, sample molecules bind to the substrate surface. Light covering a span of angles of incidence is shone on the substrate and is reflected into a detector that measures the intensity of reflected light. Binding of molecules to the surface changes the angle at which surface plasmon resonance occurs, and this change can be detected and quantified. The placement of the flow chambers during interrogation determines the regions of interest for analysis, with each region containing both a printed section and a reference section. Sensorgram data for the reaction sections can be corrected using the sensorgram data from the reference section.

In another embodiment, the spotter may be used to print in multiple adjacent locations, where one section of printed surface is directly adjacent to another section of printed surface. In a particular aspect, the second section is printed with a different substance than the first printed section. In a more particular aspect, both sections are initially printed with one or more substances in common, while only one of the sections is further printed with one or more additional substances. This can be accomplished by the method described above, where the spotter is first positioned for one or more printings, then moved in one direction so as to print the additional substance (s) only on a portion of the previous spot. This process may be reiterated as needed, thereby producing one or more strips of adjacent printings, with each printing having different layers. In this embodiment, after printing of all of the substances, the spotter may be placed so that each flow chamber is exposed to a section of surface printed with one or more substances and part of said section is printed with one or more additional surfaces. The section may be then interrogated, with one portion of the interrogated section serving as a reference for analysis of the other portion.

Figure 5:
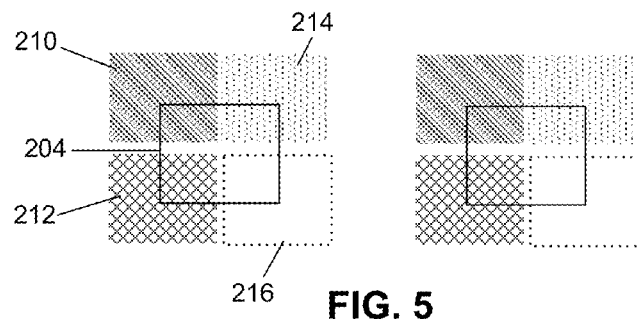
FIG. 5 is a diagram illustrating of an array printed with a spotter in accordance with an embodiment of the present disclosure, showing the arrangement of initially printed spots and successive printing locations and indicating the location of flow chambers for simultaneous interrogation.

In one aspect of this embodiment, an array can be printed where the spotter is moved in such a way after each printing so as to create clusters of multiple adjacent spots that may all be interrogated at once. A diagram of two such clusters is shown in FIG. 5. The clusters of initial printings 210-214 may be created by shifting the spotter in different successive directions. In a particular aspect, a different substance is used in each printing. In a more particular aspect, one of the shifts may be preceded by no printing or a sham printing 216 using only carrier. The spotter may then be placed so as to establish a flow chamber outline 204 that is exposed to all of the spots simultaneously. In this way all of the spots may be interrogated simultaneously, providing multiple internal referencing.

The multiple referencing approach can also be realized by using a spotter or combination of spotters, wherein the spotter used for initial printing(s) is configured to print a plurality of spots in an arrangement that facilitates simultaneous interrogation. In one embodiment, such a spotter includes groups of orifices where, when placed against a surface, every orifice is exposed to a common section of surface. In a particular embodiment, orifices are used that are roughly triangular or wedge-shaped, and are arranged in a circular array, with the apex of each wedge pointing into the center of the circle. In a more particular embodiment, such an arrangement is part of an annular spotter design. In such a design, multiple microchannels may also be contained within a larger microchannel. For example, multiple inlet microchannels, for example, 2, 3, 4, 5, 6, 7, or 8 inlet microchannels, each carrying a different substance could be within a larger microchannel that serves as the outlet microchannel. The circular array of spots resulting from printing with this spotter can then be interrogated by a different spotter having a single orifice placed in the center of the array, so that the cavity is exposed to all of the printed spots at once. Such a spotter may comprise a different annular design created by placing a narrow microchannel within a larger microchannel, where the narrow microchannel serves as the inlet microchannel.

The versatility of the spotter described above makes it possible to integrate the spotter with a variety of analysis platforms. Accordingly the present disclosure also provides a system for microassay with internal referencing. A general embodiment of the system comprises a substrate having a surface. In more specific embodiment, the surface is particularly adapted for receiving a substance needed for a particular assay, e.g. a capture substance. The system also comprises a spotter as disclosed herein, as well as a manipulator that is connected to the spotter and is capable of moving the spotter relative to the substrate. In a specific aspect the manipulator is capable of moving the spotter in at least an axis parallel to the surface of the substrate. In a more specific aspect, the manipulator can also move the spotter in an axis substantially perpendicular to the surface of the substrate. In a still more specific aspect, the manipulator is capable of moving the spotter in two axes parallel to the surface of the substrate. The system can also comprise a sensor or transducer capable of detecting a signal associated with binding of substances in a region of interest on the substrate. In a more particular embodiment, the system also includes a computer or other processing device for analyzing the signal. In a still more particular embodiment, the processing device is configured to use the signal detected in a reference section of the region of interest to correct the signal detected in a printed section.

EXAMPLES

Methods and Materials

A spotter in accordance with the above description was integrated with an SPRi platform to create a system to provide an assay for binding with interspot referencing.

The integration provided 48 isolated flow cells for the interrogation of 48 separate analytes, buffers, or other materials. Such a system is capable of eight times the throughput of existing SPRi commercial platforms with the potential to be scaled up.

In this field of art, a substrate surface coated with dextran has been used as a means to improve sensitivity and reduce non-specific adsorption. The utilization of the dextran surface enabled a much larger capture density to perform experiments in a 3-D space as opposed to a more planar coupling chemistry. The incorporation of a "spot and hop" technique as described above was used with the present system to improve the sensitivity by removing non-specific binding effects within each spot. Traditional referencing in SPRi may incorporate surrounding regions around each ROI to subtract background signal, but the "spot and hop" enables the reference space to see the same sample as the printed area for each spot addressed by the spotter. This can be extended to multiple "spot and hop" movements, which implies every step of a complex binding study could be referenced within each spot.

Example 1

Spotter-SPRi Integration

Standard spotter printheads manufactured by Wasatch Microfluidics (North Salt Lake, Utah) were used for the real-time SPRi experiments. The SPRi detector was a Proteomic Processor™ (Plexera Biosciences, LLC, Seattle, Wash.). Carboxy-methyl dextran coated (CM5) chips were acquired from Biacore/GE Healthcare (Uppsala, Sweden). Custom fixtures were adapted to the Proteomic Processor top plate to mount the spotter above the sensor platform. Positioning x-y-z stages (Edmunds Optics, Barrington, N.J.) were used to provide control of the spotter for the "spot and hop" movement. A spotter printhead was adapted to provide the fluidic control for all 48 flow channels in the spotter.

The microfluidic layout of the spotter required the samples to enter perpendicular to the microfluidic channels that carry sample to the surface. The Proteomic Processor sensor platform faced upward allowing the spotter printhead to easily integrate with the prism and chip holder. The custom fixtures and positioning stages enabled accurate retraction and horizontal movement for the spot and hop experiments as well as for removing and inserting chips.

Example 2

Response Time Experiment

Figure 6:
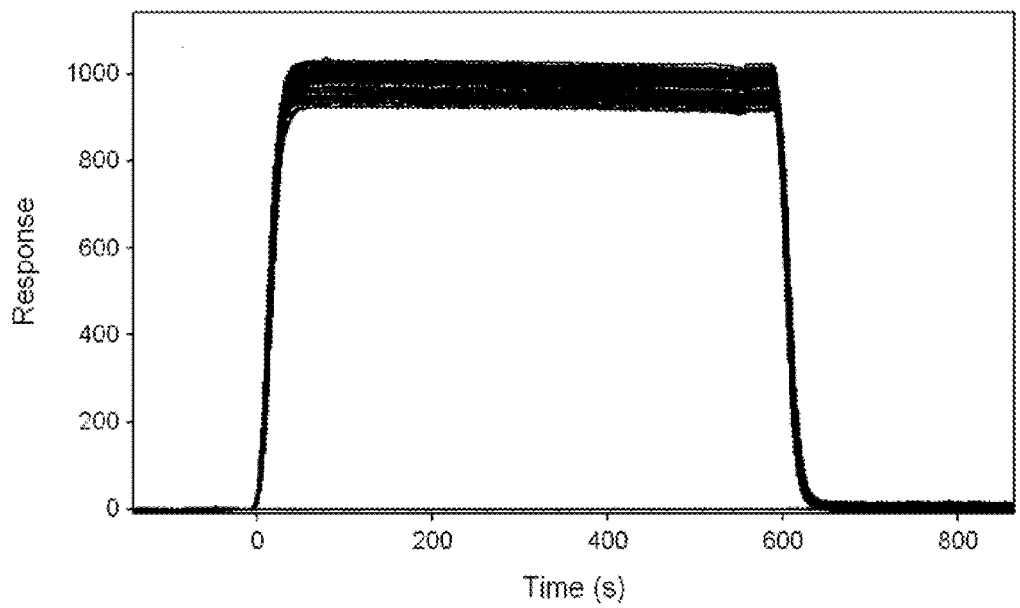
FIG. 6 is an SPRi sensorgram showing the response time of deposition of glycerol onto the sensor surface with a 48-channel spotter as in FIG. 1 in accordance with an embodiment of the present disclosure.

Visualization of the spotter-SPRi response time was accomplished by inducing a bulk refractive index change using 100% Glycerol. Running buffer (PBS, pH 4.0) was initially injected for 5 minutes at a flow rate of 150 µL/min to establish a baseline. Glycerol was then injected at the same flow rate for 10 minutes followed by buffer. The response time is illustrated by the sharpness of the curves exhibited by the sensorgram shown in FIG. 6. The rise and fall time in all 48 channels are tightly grouped for both the injection and the switch to buffer. This implies the channels were flowing evenly and arriving at the surface at virtually the same time.

Example 3

Protein A Preconcentration

Figure 7:
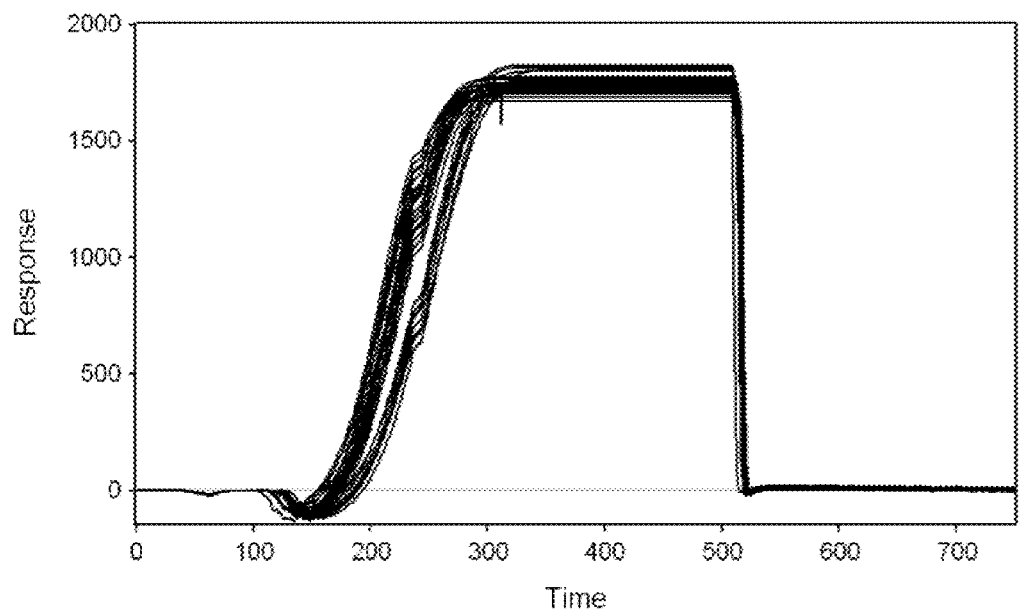
FIG. 7 is an SPRi sensorgram showing a preconcentration test with Protein A onto a dextran-coated sensor surface in accordance with an embodiment of the present disclosure.

A preconcentration experiment was performed to confirm negligible non-specific adsorption to a carboxy-methyl dextran surface (CM5). Protein A was selected as the test protein as it was used for antibody capture in other experiments. Running buffer (PBS, pH 4.0) was initially injected for 5 minutes at a flow rate of 150 µL/min to establish a baseline. Protein A at 10 µg/ml was then injected for 6 minutes, followed by buffer. The option of using a Dextran CM5 chip was of special interest in order to increase sensitivity and work with a well-established surface chemistry for the demonstration of the spot and hop referencing. A preconcentration experiment using the protein A as the prospective capture surface was first undertaken to verify the absence of non-specific adsorption to the Dextran chip. The results were similar to a preconcentration study in the first reported use of Dextran for SPRi. The injection of protein A across the unactivated Dextran surface did not retain any distinguishable response after buffer was introduced as shown in FIG. 7.

Example 4

In Situ Activation/Immobilization/Regeneration

Figure 8:
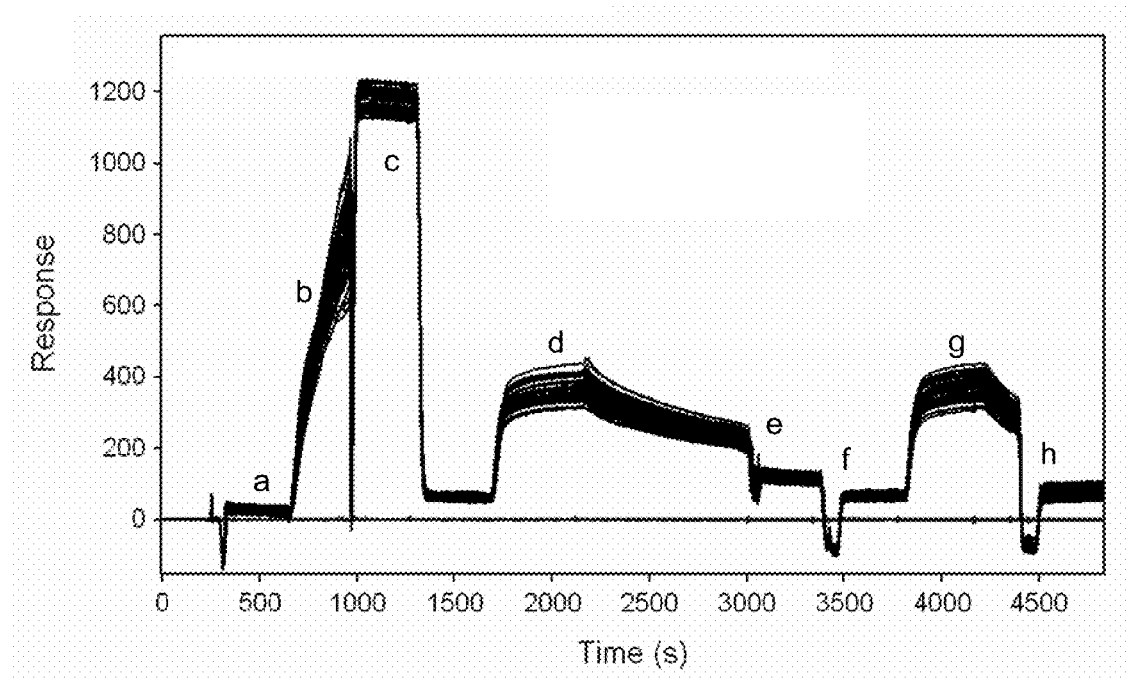
FIG. 8 is an SPRi sensorgram of activation of a dextran-coated sensor surface (a), Protein A immobilization (b), ethanolamine inactivation of the dextran surface (c), captured bovine IgG (d), regeneration of surface with HCl (e, f), second captured bovine IgG trial (g), and final HCl regeneration (h) in accordance with an embodiment of the present disclosure.

The in situ amine coupling was accomplished using a 1:10 dilution of a mixture of N-ethyl-N'-(3-dimethlyaminopropyl) carbodiimide hydrochloride (EDC) and N-hydroxysuccinimide (NHS). The mixture was injected at 150 µl/min for 6 minutes. Protein A at 10 µg/ml was then injected for 6 minutes, followed by inactivation of the ester active sites by ethanolamine (concentration) for an additional 6 minutes. Buffer was then injected for 6 minutes to stabilize the baseline prior to antibody capture. Bovine IgG at 300 nM was then injected for 10 minutes followed by PBS buffer. A regeneration step was performed using HCl at 1:1000. All regeneration injections were run for 90 seconds. A subsequent injection of HCl at 1:500 was used because the 1:1000 regeneration did not successfully return the surface to conditions prior to antibody capture. An additional bovine IgG injection at 300 nM for 8 minutes was used to verify that the surface was active. It was followed by a PBS wash and a subsequent HCl regeneration (1:500). The capture of bovine IgG (300 nM) and the subsequent regeneration of the surface was all accomplished using the custom fluidic control within the spotter-SPRi platform. A sensorgram of the entire test is shown in FIG. 8.

Example 5

Patterning and Interrogation

Figure 9:
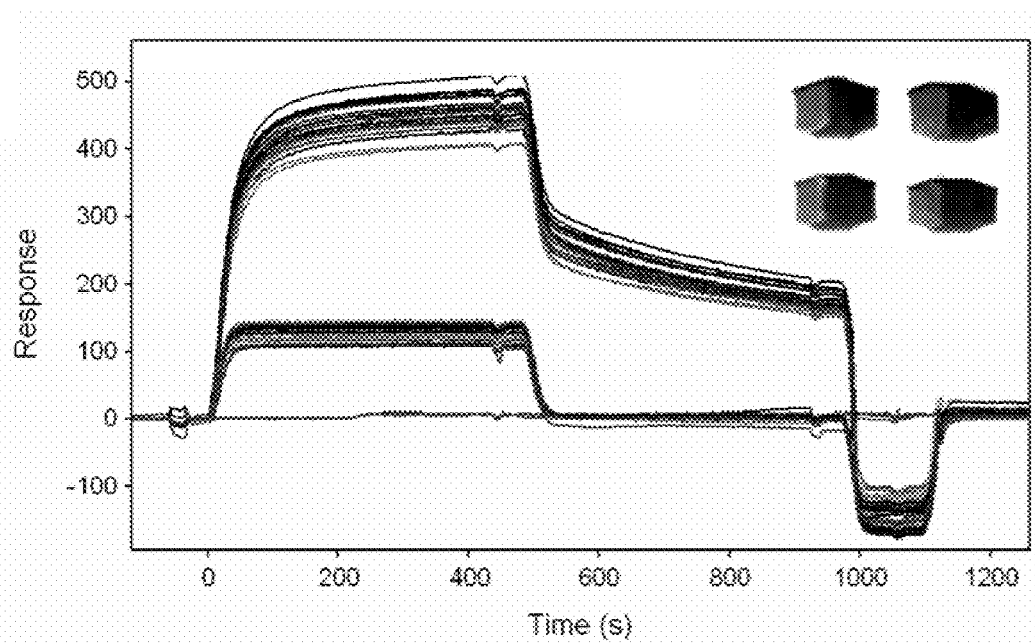
FIG. 9 is an SPRi sensorgram of captured bovine IgG on an activated dextran surface and an inactivated dextran reference surface, with sensor regions having both surfaces depicted in the inset in accordance with an embodiment of the present disclosure.
Figure 10:
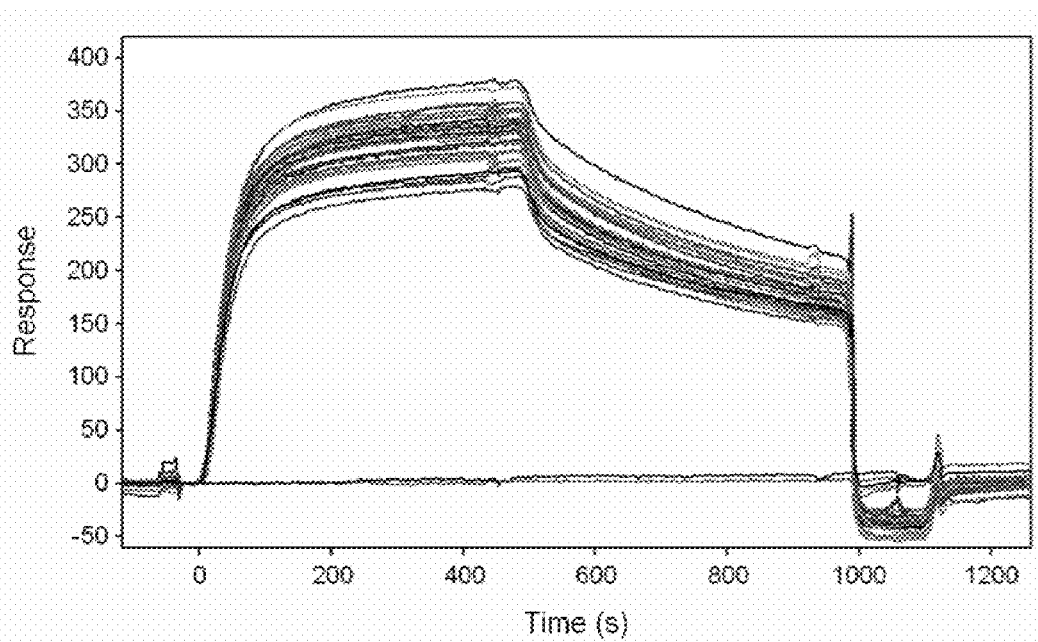
FIG. 10 is an SPRi sensorgram of captured bovine IgG (with dilute glycerol) on the activated dextran surface as in FIG. 7 that has been corrected by subtracting the non-specific response due to glycerol in reference area in accordance with an embodiment of the present disclosure.

A Protein A capture surface was immobilized using the process described in the previous section. One channel was left blank without immobilization, running only buffer. After immobilization, all liquid was removed from the spotter. The spotter tip was then retracted and moved horizontally approximately 0.5 mm. Regions of interest (ROI) were redrawn to cover each half of the spot, the protein A active region and the unactive Dextran region. PBS buffer was injected to reestablish a baseline. Bovine IgG (300 nM) was then injected in half the channels and a diluted glycerol solution (9 µl glycerol in 1500 µl buffer) was injected in the other half for 7 minutes at 150 µl/min to induce a bulk refractive index change similar to non-specific adsorption. The capture injections were followed by buffer and a subsequent regeneration step (1:500 HCl). The glycerol mixture exhibited a response similar to that of non-specific adsorption. The captured IgG signal was then referenced according to the simulated non-specific response of the glycerol mixture as shown in FIGS. 9 and 10.

The spotter-SPRi integrated platform illustrates the potential for a parallel high-throughput detection platform. The ability to perform 48 separate experiments simultaneously not only provides the potential for more statistically relevant data, but it also provides the user options. Whether it is screening 48 different antibodies or exploring 48 different buffer conditions, the parallel capability of the spotter can enhance SPRi six times (or more) over existing commercial SPR platforms. The spotter configuration also makes it a good candidate for other SPRi sensor platforms. It can be applied horizontally or vertically depending on the configuration of the SPR sensor.

The spotter response time is encouraging for use in categorizing binding kinetics. The sharpness in response curves due to large refractive index changes demonstrated the spotter flow performance was consistent across all 48 channels. The spotter performance was also confirmed in the in situ activation, immobilization, and regeneration experiments. The rise and fall times were consistent and within seconds of each other across the spots. More importantly, the experiments demonstrated that the spotter functioned well as a complete flowcell for steps that are traditionally performed in situ in other commercial instruments.

The capability of using existing dextran CM5 chips is also valuable as the surface binding capacity can be greatly improved for SPRi detection platforms, which have not traditionally used dextran. The dextran chip coupled with interspot referencing can be an effective tool for the analysis of complex samples using a robust surface chemistry. Current referencing techniques do not typically account for local intensity changes across the spot. The interspot referencing creates local inline referencing that could be used in more complicated immobilization studies. The spotter could also move an additional two times in the vertical direction and then back horizontally to provide to more local referencing sites. This would maintain within each spot local referencing for up to two more immobilized molecules. It not only frees up additional channels that would normally be used as references for each immobilization, but also provides a more accurate reference as each spot has its own local reference.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. For example, systems in accordance with the present invention may be realized by integrating the spotter disclosed herein with other sensing and analysis platforms capable of handling microarrays. Accordingly, it is not intended that the invention be limited, except as by the claims set forth below.

What is claimed is:

1. A method for patterning a surface for a microassay, comprising:
   a) providing a spotter including at least one fluid pathway adapted to provide a printing cavity having a printing orifice and an interrogation cavity having an interrogation orifice, both the printing orifice and the interrogation orifice being configured to form a seal with the surface;
   b) placing the spotter against the surface so as to seal the printing orifice to the surface and form a printing flow chamber defined by the printing cavity and the surface;
   c) flowing a fluid through the printing flow chamber so as to print a spot onto the surface;
   d) relocating the spotter along the surface over a distance and in a direction so that the interrogation orifice overlaps both a portion of the spot and an adjacent unprinted space of the surface;
   e) placing the spotter against the surface so as to seal the interrogation orifice to the surface to form an interrogation flow chamber defined by the interrogation cavity and a second location on the surface, said second location being positioned over both a portion of the spot and an adjacent unprinted space; and
   f) flowing a second fluid through the interrogation flow chamber so as to generate contact between the second fluid and both the portion of the spot and the unprinted space.

2. The method of claim 1, wherein the fluid includes a capture substance and the second fluid is a sample fluid that is different than the fluid containing the capture substance.

3. The method of claim 1, wherein the fluid is a sample fluid and the second fluid includes a capture substance and is different than the sample fluid.

4. The method of claim 1, further comprising:
   a) measuring a sample signal created by reaction between a capture substance and an analyte, one of which is present in the fluid and the other of which is present in the second fluid;
   b) measuring a reference signal from the unprinted space; and
   c) correcting the sample signal through an operation based on the reference signal.

5. The method of claim 4, wherein the operation comprises subtracting a value associated with the reference signal from a value associated with the sample signal.

6. The method of claim 1, wherein a plurality of capture substances are sequentially flowed through the printing flow chamber before the second fluid is flowed through the interrogation flow chamber, and wherein the second fluid is a sample fluid.

7. The method of claim 1, wherein the distance is about one-half of the size of the spot.

8. The method of claim 1, wherein the distance is such that the interrogation flow chamber includes substantially equal areas of spot and unprinted space.

9. The method of claim 1, wherein the fluid is flowed through the printing flow chamber more than once.

10. The method of claim 1, wherein the second fluid is flowed through the interrogation flow chamber more than once.

11. The method of claim 1, wherein the recited steps are repeated at least once.

12. The method of claim 1, wherein the spotter includes a plurality of fluid pathways, each comprising a printing cavity that includes a printing orifice adapted to form a seal with the surface.

13. The method of claim 12, wherein at least two of the plurality of fluid pathways are used simultaneously on the surface to form spots.

14. The method of claim 1, wherein the printing cavity and printing orifice are the same structure as the interrogation cavity and interrogation orifice, respectively.

15. A method for performing a microassay with internal referencing, comprising:
   a) providing a spotter comprising a fluid pathway including a cavity that comprises an orifice adapted to form a seal with the surface;
   b) placing the spotter against the surface so as to seal the orifice to the surface and form a first printing flow chamber defined by the cavity and the surface;
   c) flowing a first fluid containing a first substance through the first printing flow chamber so as to print a first spot of the first substance onto the surface;
   d) relocating the spotter along the surface over an adjacent space relative to the first spot;
   e) placing the spotter against the surface so as to seal the orifice to the surface and form a second printing flow chamber defined by the cavity and the surface;
   f) flowing a second fluid containing a second substance through the second printing flow chamber so as to print the second substance to form a second spot;
   g) relocating the spotter along the surface so that the orifice overlaps both a portion of the first spot and a portion of the second spot;
   h) placing the spotter against the surface so as to seal the orifice to the surface and form an interrogation flow chamber defined by the cavity and the surface; and i) flowing a sample fluid through the interrogation flow chamber so that the sample fluid encounters both at least the portion of the first spot and the portion of the second spot.

16. The method of claim 15, wherein the spotter includes a plurality of fluid pathways, each comprising a cavity that includes an orifice adapted to form a seal with the surface.

17. The method of claim 16, wherein at least two of the plurality of fluid pathways are used simultaneously on the surface to form spots.

18. The method of claim 15, wherein at least two of the first printing flow chamber, the second printing flow chamber, and the interrogation flow chamber are the same.

19. The method of claim 15, wherein at least two of the first printing flow chamber, the second printing flow chamber, and the interrogation flow chamber are different.

20. The method of claim 15, wherein the second printing flow chamber also acts as an interrogation flow chamber with respect to the first spot.

21. The method of claim 15, wherein the fluid in the interrogation flow channel also encounters an adjacent unprinted space.

22. A system for performing a microassay with internal referencing, comprising:
    a) a spotter comprising a fluid pathway including a cavity with an orifice adapted to form a seal with a surface and to form a spot on the surface within the orifice;
    b) a manipulator operably connected to the spotter and adapted to seal, relocate, and re-seal the orifice against the surface, said re-seal of the orifice on the substrate being carried out by relocating the cavity from a location of the seal over a distance and in a direction so that the orifice overlaps both a portion of the spot and an adjacent unprinted space of the surface; and
    c) a sensor and processor capable of detecting a sample signal created by reaction of a capture substance with an analyte of a sample fluid and situated to detect the sample signal from said reaction occurring in a region at or near a location where the orifice is sealable against the surface, wherein the sensor and processor are adapted to measure the sample signal, measure a reference signal from the adjacent unprinted space, and correct the sample signal through an operation based on the reference signal.

23. The system of claim 22, further comprising a substrate having a surface adapted for receiving or binding a capture substance.

24. The system of claim 22, wherein the manipulator is configured for moving the spotter in at least two axes relative to the surface.

25. The system of claim 24, wherein the at least two axes includes an axis substantially parallel to the surface.

26. The system of claim 24, wherein the at least two axes includes an axis substantially perpendicular to the surface.

27. The system of claim 22, wherein the system includes a plurality of fluid pathways, each comprising a cavity that includes an orifice adapted to form a seal with the surface.

28. The system of claim 27, wherein at least two of the plurality of fluid pathways are used simultaneously on the surface to form spots.

29. The system of claim 22, wherein the surface is a sensor.

30. A method of performing a microassay on surface, comprising:
    a) providing a spotter including at least one fluid pathway adapted to provide a printing cavity having a printing orifice and an interrogation cavity having an interrogation orifice, both the printing orifice and the interrogation orifice being configured to form a seal with the surface;
    b) placing the spotter against the surface so as to seal the printing orifice to the surface and form a printing flow chamber defined by the printing cavity and the surface;
    c) flowing a fluid including a capture substance through the printing flow chamber so as to print a spot including the capture substance onto the surface;
    d) relocating the spotter along the surface over a distance and in a direction so that the interrogation orifice overlaps both a portion of the spot and an adjacent unprinted space of the surface;
    e) placing the spotter against the surface so as to seal the interrogation orifice to the surface to form an interrogation flow chamber defined by the interrogation cavity and a second location on the surface, said second location being positioned over both a portion of the spot and an adjacent unprinted space; and
    f) flowing a sample fluid through the interrogation flow chamber so as to generate contact between the second fluid and both the portion of the spot and the unprinted space.

31. The method of claim 30, further comprising:
    a) measuring a sample signal created by reaction between the capture substance and an analyte of the sample fluid;
    b) measuring a reference signal from the unprinted space; and
    c) correcting the sample signal through an operation based on the reference signal.

32. The method of claim 15, wherein the adjacent space is situated partially over the first spot.

* * * * *